United States Patent [19]

Bourguignon et al.

[11] Patent Number: 4,810,705

[45] Date of Patent: Mar. 7, 1989

[54] TRIAZOLO [3,4-B]PYRIDAZINES, PROCESS FOR THEIR PREPARATION AND PHARMACEUTICAL COMPOSITIONS CONTAINING THEM

[75] Inventors: Jean-Jacques Bourguignon, Hipsheim; Jean-Pierre Chambon, Montarnaud; Camille-Georges Wermuth, Strasbourg, all of France

[73] Assignee: Sanofi, Paris, France

[21] Appl. No.: 62,341

[22] Filed: Jun. 10, 1987

Related U.S. Application Data

[63] Continuation of Ser. No. 717,458, Mar. 29, 1985, abandoned.

[30] Foreign Application Priority Data

Mar. 3, 1984 [FR] France .................. 84 05086

[51] Int. Cl.$^4$ .................. C07D 487/04; A61K 31/50
[52] U.S. Cl. .................. 514/248; 544/236;
544/224; 544/239; 549/323; 549/549
[58] Field of Search .................. 514/248; 544/236

[56] References Cited

U.S. PATENT DOCUMENTS

| | | | |
|---|---|---|---|
| 4,062,958 | 12/1977 | Allen, Jr. et al. | 514/248 |
| 4,112,095 | 9/1978 | Allen, Jr. et al. | 544/236 |
| 4,230,705 | 10/1980 | Allen, Jr. et al. | 544/236 |
| 4,260,755 | 4/1981 | Moran et al. | 544/236 |
| 4,515,791 | 5/1985 | Allen, Jr. et al. | 544/236 |
| 4,748,179 | 5/1988 | Braestrup et al. | 514/292 |
| 4,748,180 | 5/1988 | Petersen et al. | 514/292 |
| 4,767,765 | 8/1988 | Albright et al. | 544/236 |

FOREIGN PATENT DOCUMENTS 2741763 3/1978 Fed. Rep. of Germany .
3217325 11/1983 Fed. Rep. of Germany .
839020 6/1960 United Kingdom .

OTHER PUBLICATIONS

Furlan et al., *Monatsh. Chem.*, 105, pp. 834–839 (1974).
Morrison and Boyd, "Organic Chemistry", 3rd Ed., Allyn and Bacon (1973), pp. 632, 1015.
Bown et al., *J. Org. Chem.*, vol. 45, pp. 2320–2324 (1980).

*Primary Examiner*—Donald G. Daus
*Assistant Examiner*—E. Bernhardt
*Attorney, Agent, or Firm*—Foley & Lardner, Schwartz, Jeffery, Schwaab, Mack, Blumenthal & Evans

[57] ABSTRACT

The invention relates to 1,2,4-triazolo [4,3-b]pyridazines substituted in the 7-position of formula:

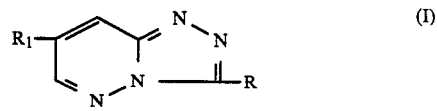

in which R represents hydrogen, a lower alkyl group, a phenyl group, a chlorophenyl group or a benzyl group and $R_1$ represents a phenyl, halogenophenyl, trifluoromethylphenyl, lower alkyl-phenyl or lower alkoxy-phenyl group or a phenyl-lower alkyl group, or one of its pharmaceutically acceptable salts.

Said compounds antagonize the effects of benzodiazepines and therefore are useful as antidotes in the abuse of benzodiazepines and compounds acting on benzodiazepine receptors.

10 Claims, No Drawings

TRIAZOLO [3,4-B]PYRIDAZINES, PROCESS FOR THEIR PREPARATION AND PHARMACEUTICAL COMPOSITIONS CONTAINING THEM

This application is a continuation of application Ser. No. 717,458 now abandoned, filed Mar. 29, 1985.

The present invention relates to triazolo[4,3-b]pyridazines carrying an optionally substituted phenyl group or a phenyl-lower alkyl group in the 7-position, a process for their preparation and pharmaceutical compositions in which the said triazolopyridazines are present as active ingredients.

Triazolo[4,3-b]pyridazines carrying an optionally substituted phenyl group in the 6-position are known in the literature.

German Patent Application No. 2 741 763 describes 6-phenyl-1,2,4-triazolo[4,3-b]pyridazines optionally carrying alkyl groups in the 3-, 7- and 8-positions.

German Patent Application No. 3 217 325 also describes 6-phenyl-1,2,4-triazolo[4,3-b]pyridazines, but these are substituted in the 3-position by a free amino group.

The compounds of the two patent applications mentioned above possess an anxiolytic, sedative and anticonvulsant activity which was demonstrated, in the case of the compounds of German Patent application No. 2 741 763, by comparison with a benzodiazepine, namely chlordiazepoxide.

It has now been found, unexpectedly, that certain triazolo[4,3-b]pyridazines carrying an optionally substituted phenyl group or a phenyl-lower alkyl group in the 7-position antagonize the effects of benzodiazepine and are therefore useful as antidotes in the abuse of benzodiazepines and compounds acting on benzodiazepine receptors.

Thus, according to one of its aspects, the present invention relates to 1,2,4-triazolo[4,3-b]pyridazines substituted in the 7-position, of the formula:

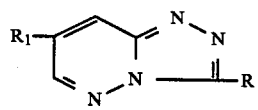
(I)

in which R represents hydrogen, a lower alkyl group, a phenyl group, a chlorophenyl group or a benzyl group and $R_1$ represents a phenyl group, a phenyl substituted by a halogen atom, a phenyl substituted by a trifluoromethyl group, a phenyl substituted by a lower alkyl, a phenyl substituted by a lower alkoxy, or a phenyl-lower alkyl group, and also to their pharmaceutically acceptable salts.

The term "lower alkyl", as used here, denotes the radical of a saturated aliphatic hydrocarbon containing up to 6 carbon atoms, such as methyl, ethyl, n-propyl, n-hexyl or isobutyl.

The term "lower alkoxy" denotes a hydroxyl in which the hydrogen atom has been replaced by a lower alkyl group as defined above.

According to another aspect, the present invention relates to a process for the preparation of the 7-phenyl-1,2,4-triazolo[4,3-b]pyridazines of the formula (I) above and their pharmaceutically acceptable salts, wherein the starting material used is a compound of the formula:

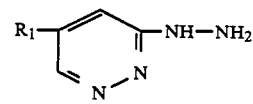
(II)

in which $R_1$ is as defined above. In a first variant of the process, the product (II) is treated with an orthoester of the formula:

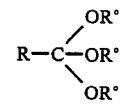

in which R is as defined above and R° represents a methyl or ethyl group, in an organic solvent, at a temperature of 50° to 175° C., and, if appropriate, the product thus obtained is converted to its pharmaceutically acceptable salts.

The organic solvent used is preferably an alcohol such as methanol, ethanol, isopropanol, n-butanol, n-pentanol or the like.

In a preferred embodiment, after heating under reflux in n-butanol for 5–9 hours, the reaction is stopped and the final product is isolated in the form of the free base simply by filtration, and purified by the known techniques.

In a second variant, the hydrazine (II) is treated with the aldehyde RCHO to form the corresponding hydrazone, which, on heating in the presence of an oxidizing agent, namely diethyl azidodicarboxylate, leads to the product (I).

The hydrazone is formed by heating the reactants in a suitable solvent, namely methylene chloride, methanol or a mixture of the 2 solvents, at the reflux temperature. The crude hydrazone obtained by evaporation of the reaction mixture to dryness is dissolved in n-butanol, treated with excess diethyl azidodicarboxylate and heated under reflux for 3 to 10 hours. The product is isolated in the form of the free base by evaporation of the solvent, and purified by the known techniques.

The starting compounds of the formula (II) are prepared from a pyridazin-3-one substituted in the 5-position, of the formula:

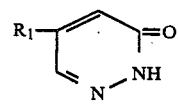
(III)

in which $R_1$ is as defined above, by reaction with phosphorus oxychloride; after treatment with an alkali metal hydroxide, preferably sodium hydroxide, the 3-chloropyridazine of the formula:

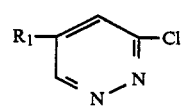
(IV)

in which $R_1$ is as defined above, is isolated and the product thus obtained is treated with excess hydrazine hydrate at a temperature of 60° to 90° C., under an inert atmosphere, for a period of 4 to 8 hours. The product of the formula (II) is isolated by the conventional methods.

The compounds of the formulae (II) and (IV) are new and represent a further subject of the present invention.

The compounds of the formula (III) used as starting materials in the process of the present invention are in general new; they can be prepared in accordance with the method described by J. J. BOURGUIGNON and C. G. WERMUTH (J. Org. Chem. 1981, 46, 4889–4894) for the preparation of 5-phenylpyridazin-3-one (formula III, $R_1$=phenyl), the phenylacetaldehyde being replaced by an acetaldehyde substituted by $R_1$ ($R_1$: other than phenyl).

The examples which follow illustrate the invention without however implying a limitation.

PREPARATION 1

(a) Methyl 3-(4-methoxyphenyl)-2,3-epoxypropanoate 13.6 g of p-methoxybenzaldehyde are added to a solution of sodium methylate in methanol (obtained from 3.5 g of sodium and 50 ml of methanol), cooled to −10° C., and 10.85 g of methyl chloroacetate are then added dropwise. The mixture is stirred for 2 hours at −5° C. and then for 3 hours at room temperature.

The reaction mixture is poured onto 200 g of ice containing 1.15 ml of acetic acid. The solid is filtered off, washed with water and dried in vacuo. Weight: 16 g.

(b) Sodium 3-(4-methoxyphenyl)-2,3-epoxypropionate

A solution of sodium methylate in methanol, obtained from 1.54 g of sodium and 21.5 ml of methanol, is added slowly, at +5° C., to a mixture of 13.5 g of the product obtained under (a) and 82 ml of benzene. 1.36 ml of water are then added, followed by 60 ml of ether. The mixture is left to stand and the solid is then filtered off. After drying, 12.3 g of the expected product are obtained.

(c) (4-Methoxyphenyl)acetaldehyde 2.8 g of acetic acid are added to 10 g of the sodium salt obtained above, in 50 ml of benzene, and the mixture is heated under reflux for 2 hours 30 minutes.

After cooling, 100 ml of benzene and 15 ml of water are added. The organic layer is separated off and washed with water and the solution is dried and evaporated to dryness. This gives 5 g of the expected product.

(d) 4-Hydroxy-3-(4-methoxyphenyl)but-3-en-4-olide 5 g of 4-(methoxyphenyl)acetaldehyde are added to a solution of 3.22 g of glyoxylic acid and 4.3 g of morpholine hydrochloride in 30 ml of dioxane. The mixture is stirred for 1 hour at room temperature and then heated for 24 hours under reflux. The solvent is evaporated off and the residue is taken up in water. The solid is filtered off and dried in vacuo. This gives 6.2 g of the expected product.

Thin layer chromatography: Rf=0.67 (ethyl acetate/hexane, 1/1 vol/vol).

(e) 5-(4-Methoxyphenyl)-2H-pyridazin-3-one

A mixture of 4.1 g of the product obtained above and 1.1 g of hydrazine hydrate in 60 ml of ethanol are heated under reflux for 1 hour 30 minutes.

The mixture is left to stand and the solid is then filtered off and dried. This gives 2.82 g of the expected product.

Thin layer chromatography: Rf=0.15 (ethyl acetate/hexane, 1/1 vol/vol).

PREPARATIONS 2 to 8

The following are obtained using the procedure described in Preparation 1:
5-(4-chlorophenyl)-2H-pyridazin-3-one (2);
5-(3-chlorophenyl)-2H-pyridazin-3-one (3);
5-(2-chlorophenyl)-2H-pyridazin-3-one (4);
5-(3-trifluoromethylphenyl)-2H-pyridazin-3-one (5);
5-(4-methylphenyl)-2H-pyridazin-3-one (6);
5-benzyl-2H-pyridazin-3-one (7);
5-(2-phenylethyl)-2H-pyridazin-3-one (8).

EXAMPLE I (a) 3-Chloro-5-(4-methoxyphenyl)pyridazine 2.7 g of 5-(4-methoxyphenyl)-2H-pyridazin-3-one and 19.9 g of phosphorus oxychloride are heated at 80° C. for 4 hours, with stirring.

The mixture is then poured slowly into iced water, with stirring, after which the resulting mixture is rendered alkaline with a 20% sodium hydroxide solution. The precipitate is filtered off, washed with a large quantity of water and then dried. This gives 2.4 g of the expected product.

Thin layer chromatography: Rf=0.2 (ethyl acetate/hexane, 1/3 vol/vol).

(b) 3-Hydrazino-5-(4-methoxyphenyl)pyridazine

A mixture of 2.3 g of the product obtained above and 13.6 g of hydrazine hydrate is heated at 80° C. under a nitrogen atmosphere for 6 hours.

Water is added and the solid which has separated out is filtered off. After drying, 2.8 g of the expected product are obtained.

NMR spectrum: run in solution in deuterochloroform. 3H at 3.8 ppm (singlet)-3H at 4.3 ppm (broadened singlet)-4H at 7.0–7.5 ppm (AB system, $J_{AB}$=9 Hz)-1H at 7.1 ppm (doublet)- 1H at 8.7 ppm (doublet, J=2 Hz).

EXAMPLES II to IX

The following are obtained by reacting the compounds described in Preparations 2 to 8 and 5-phenyl-2H-pyridazin-3-one (J. Org. Chem. 1981, 46, 4893) with phosphorus oxychloride as described in Example Ia), and treating the resulting products as described in Example Ib):

EXAMPLE II (a) 3-Chloro-5-(4-chlorophenyl)pyridazine.
(b) 5-(4-Chlorophenyl)-3-hydrazinopyridazine.

EXAMPLE III (a) 3-Chloro-5-(3-chlorophenyl)pyridazine.
(b) 5-(3-Chlorophenyl)-3-hydrazinopyridazine.

EXAMPLE IV (a) 3-Chloro-5-(2-chlorophenyl)pyridazine.
(b) 5-(2-Chlorophenyl)-3-hydrazinopyridazine.

EXAMPLE V (a) 3-Chloro-5-(3-trifluoromethylphenyl)pyridazine.
(b) 3-Hydrazino-5-(3-trifluoromethylphenyl)pyridazine.

EXAMPLE VI (a) 3-Chloro-5-(4-methylphenyl)pyridazine.
(b) 3-Hydrazino-5-(4-methylphenyl)pyridazine.

EXAMPLE VII (a) 3-Chloro-5-benzylpyridazine.
(b) 5-Benzyl-3-hydrazinopyridazine.

EXAMPLE VIII (a) 3-Chloro-5-(2-phenylethyl)pyridazine.
(b) 3-Hydrazino-5-(2-phenylethyl)pyridazine.

EXAMPLE IX (a) 3-Chloro-5-phenylpyridazine.
(b) 3-Hydrazino-5-phenylpyridazine.

EXAMPLE 1

7-(4-Methoxyphenyl)-3-methyl-1,2,4-triazolo[4,3-b]pyridazine. (SR 95287)

A mixture of 1.9 g of 3-hydrazino-5-(4-methoxyphenyl)pyridazine and 2.85 g of ethyl orthoacetate in 13.7 ml of n-butanol is heated under reflux for 7 hours.

After cooling, the crystals which have separated out are filtered off and dried in vacuo. This gives 1.43 g of the expected product; melting point: 228° C.

EXAMPLE 2

7-Phenyl-1,2,4-triazolo[4,3-b]pyridazine. (SR 95194)

The procedure of Example 1 is followed using 3-hydrazino-5-phenylpyridazine and ethyl orthoformate as the starting materials; melting point: 180° C.

The products (I) collated in Table I are obtained by following the procedure of Example 1 but varying the 3-hydrazinopyridazine used as the starting material.

TABLE I

| Example No. | Product SR | No. | $R_1$ | Melting point (solvent) |
|---|---|---|---|---|
| 3 | 95 | 195 | phenyl | 216° C. (n-butanol) |
| 4 | 95 | 252 | benzyl (phenyl–CH₂–) | 114° C. (n-butanol) |
| 5 | 95 | 410 | phenyl–CH₂–CH₂– | 142° C. (isopropanol) |
| 6 | 95 | 370 | H₃C–phenyl– | 196° C. (n-butanol) |
| 7 | 95 | 437 | 2-chlorophenyl | 198° C. (ethyl acetate) |
| 8 | 95 | 398 | 3-chlorophenyl | 200° C. (ethanol) |
| 9 | 95 | 369 | 4-chlorophenyl | 238° C. (ethanol) |
| 10 | 95 | 533 | 3-(trifluoromethyl)phenyl | 188° C. (ethanol) |

EXAMPLE 11

7-Phenyl-3-benzyl-1,2,4-triazolo[4,3-b]pyridazine. (SR 95491)

A solution of 5 g of 3-hydrazino-5-phenylpyridazine in 150 ml of dichloromethane is mixed with a solution of 3.5 ml of phenylacetaldehyde in 100 ml of methanol and the mixture is then heated at 60° C. for 3 hours.

The mixture is evaporated to dryness in vacuo, the residue is then taken up in 250 ml of n-butanol, and 5.5 ml of diethyl azidodicarboxylate are added. The resulting mixture is heated under reflux for 7 hours and the solvent is then evaporated off in vacuo.

The residue is purified by column chromatography to give 2.5 g of the expected product; melting point = 140° C.

The products (I) collated in Table II are obtained by following the procedure of Example 11 but replacing the phenylacetaldehyde by benzaldehyde or chlorobenzaldehyde.

TABLE II

| Example No. | Product SR | No. | R | Melting point (solvent) |
|---|---|---|---|---|
| 12 | 95 | 494 | phenyl | 210° C. (isopropanol) |
| 13 | 95 | 492 | 4-chlorophenyl | 222° C. (ethanol) |

The compounds according to the invention were studied for their therapeutic properties.

The 1,2,4-triazolo[4,3-b]pyridazines of the present invention, substituted in the 7-position, antagonize the effects of benzodiazepines both in vitro and in vivo.

ABILITY OF THE DERIVATIVES TO DISPLACE TRITIATED FLUNITRAZEPAM FROM THE BENZODIAZEPINE RECEPTOR

The studies were carried out on synaptic preparations of rat brain in accordance with the method described by Squives and Braestrup (Nature, 1977, 266, pages 732 to 734) and Möhler and Okada (Science, 1977, 198, pages 849 to 851).

The tritiated flunitrazepam (60 Ci/mM) was used at a final concentration of 1.1 nM. The results obtained with various products of the invention are shown in Table III and are expressed as median effective concentration ($IC_{50}$) in $\mu M$.

TABLE III

| Product SR No. | $IC_{50}$ |
| --- | --- |
| 95 195 | 9 |
| 95 252 | 27 |
| 95 398 | 2.6 |
| 95 194 | 49 |
| 95 533 | 2.9 |
| 95 491 | 4.5 |
| 95 494 | 50 |

The products according to the invention are able to displace the tritiated flunitrazepam in vitro at concentrations varying from 2.6 to 50 $\mu M$. They are therefore capable of binding with the benzodiazepine receptor.

ABILITY OF THE DERIVATIVES TO ANTAGONIZE THE PHARMACOLOGICAL PROPERTIES OF BENZODIAZEPINES (a) Myorelaxant properties.

The studies were carried out by means of the traction test (J. R. Boissier et al., Archives Internationales de Pharmacodynamie, 1961, 135, pages 29–49). This test determines the ability of mice, placed with the front paws on a horizontally stretched wire, to grip with the back paws. The animals which have not brought the back paws onto the wire in less than 5 seconds are considered to be in a state of myorelaxation.

The products are administered 15 minutes before the intraperitoneal injection of a dose of 3 mg/kg of diazepam and the test is performed 60 minutes after administration of the product to be studied. The study was carried out on groups of 10 mice per dose.

The results obtained with various products of the invention are shown in Table IV.

TABLE IV

| Product SR No. | Antagonism of the myorelaxation 50% effective dose or effect (dose) |
| --- | --- |
| 95 195 | $ED_{50}$ = 26 mg/kg |
| 95 398 | $ED_{50}$ = 20 mg/kg |
| 95 533 | 100% antagonism at 100 mg/kg |

(b) Anxiolytic activity.

The studies were carried out on rats in the approach-avoidance conflict test (L. Cook and A. B. Davidson, Effects of behaviorally active drugs in a conflict-punishment procedure in rats. In: The Benzodiazepines, S. Garattini, E. Mussini and L. O. Randall, editors, Raven Press, New York, 1973, 327–345).

A representative product of the invention, SR 95 195, was administered intraperitoneally 60 minutes before an anxiolytic dose of diazepam (4 mg/kg i.p.). The test was performed 30 minutes after administration of the diazepam.

The results obtained as a function of the dose of SR 95 195 administered are as follows:

| Dose of product | % antagonism |
| --- | --- |
| 1.25 mg/kg | 26% |
| 6.25 mg/kg | 74% |
| 25 mg/kg | 100% |

Which demonstrates the ability of the product to antagonize the anxiolytic effect of diazepam according to an effect proportional to the dose.

The products according to the invention are therefore characterized by their ability to antagonize the myorelaxant effect and the anxiolytic effect of a benzodiazepine. By contrast, the 6-phenyl-1,2,4-triazolo[4,3-b]pyridazines described in German Patent Application No. 2 741 763, tested under the same conditions, potentiate the myorelaxant and anxiolytic effects of diazepam.

Furthermore, the products according to the invention were studied for their ability to reduce the food intake of fasted rats.

The studies were carried out on isolated female rats (200 to 240 g) trained to consume their food during a period of 4 hours per day. On the day of the test, 60 minutes before the food is provided, the animals receive either the product to be studied or the vehicle of administration. The quantity of food ingested during the first hour is determined.

The table below shows the results obtained with the compound SR 95 195 administered orally at a dose of 40 mg/kg. The values shown in the table are the mean values for groups of 6 rats.

| Product administered | Food intake in g | % variation relative to the control animals |
| --- | --- | --- |
| Vehicle (5% gum arabic) | 17.6 ± 1.3 | |
| SR 95 195 | 8.6 ± 1.5 | −51%++ |

++p < 0.01, Student's test

Finally, the products of the invention were studied for their toxicity.

The studies were carried out on groups of 5 female Charles River mice of the CD1 strain, weighing between 20 and 24 g. The products were administered orally, diluted in 5% gum arabic. The acute toxicity was recorded during the 72 hours following administration of the product.

The results below (percentage of dead animals) were obtained as a function of the dose administered.

| Product SR No. | % toxicity | | |
| --- | --- | --- | --- |
| | 250 mg/kg | 500 mg/kg | 1000 mg/kg |
| 95 194 | 0 | 0 | 100 |
| 95 195 | 0 | 0 | 80 |
| 95 252 | 0 | 0 | 100 |
| 95 410 | 0 | 0 | 0 |
| 95 287 | 0 | 0 | 0 |
| 95 370 | 40 | 100 | 100 |
| 95 437 | 0 | 0 | — |
| 95 398 | 0 | 0 | — |
| 95 369 | 0 | 100 | 100 |
| 95 442 | 0 | 0 | — |
| 95 494 | 0 | 0 | — |
| 95 492 | 0 | 0 | — |

The lethal doses of these derivatives are considerably higher than their active doses in the tests previously described.

The products according to the invention have valuable pharmacological properties and a low toxicity. Consequently, they can be used in human therapy for the treatment of psychic, neurological or neuromuscular complaints.

In particular, they can be used for the treatment of vigilance disorders and disorders of eating behavior. They can also be used as antidotes in cases of benzodiazepine intoxication. In addition, they can be used in association with antiparasitic products in order to suppress their depressant effects on the central nervous system.

According to another aspect, the present invention therefore relates to pharmaceutical compositions in which the compounds of the formula (I) are present as active ingredients.

The pharmaceutical compositions of the present invention can be presented in forms suitable for administration in therapy, such as ordinary tablets, coated tablets, ordinary capsules, gelatin capsules, powders, granules, suspensions or syrups for oral administration, suppositories for rectal administration and sterile solutions for parenteral administration.

The quantity of active principle can vary between 1 and 250 mg of active principle per dosage unit, according to whether this unit is intended for oral, parenteral or rectal administration, but the said quantity can be as much as 1000 mg in the case of a preparation for slow intravenous infusion.

In the dosage units, the active ingredient can be by itself or mixed with the conventional pharmaceutical vehicles or excipients such as, for example, distilled water, aqueous solution for injectable preparations, starch, talc, magnesium stearate, polyvinylpyrrolidone, alginic acid, colloidal silica, sodium chloride, titanium dioxide, cocoa butter, sweeteners and the like.

As an example of a pharmaceutical composition, gelatin capsules based on one of the compounds of Examples 1 to 13, having the following composition:
active principle: 50 mg
lactose: 85 mg
magnesium stearate: 5 mg
are prepared by intimately mixing batches of the above ingredients and pouring the mixture into hard gelatin capsules.

What is claimed is:

1. A 1,2,4-triazolo[4,3-b]pyridazine substituted in the 7-position, of the formula:

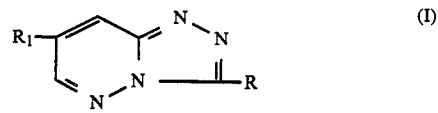

in which R represents hydrogen, a lower alkyl group, a phenyl group, a chlorophenyl group or a benzyl group and $R_1$ represents a phenyl, halogenophenyl, trifluoromethylphenyl, lower alkyl-phenyl or lower alkoxy-phenyl group or a phenyl-lower alkyl group, provided that when R is hydrogen, $R_1$ is not concurrently benzyl or one of its pharmaceutically acceptable salts.

2. 7-Phenyl-3-methyl-1,2,4-triazolo[4,3-b]pyridazine or one of its pharmaceutically acceptable salts.

3. 7-(3-Chlorophenyl)-3-methyl-1,2,4-triazolo[4,3-b]pyridazine or one of its pharmaceutically acceptable salts.

4. 7-Trifluoromethylphenyl)-3-methyl-1,2,4-triazolo[4,3-b]pyridazine or one of its pharmaceutically acceptable salts.

5. 7-Phenyl-3-benzyl-1,2,4-triazolo[4,3-b]pyridazine or one of its pharmaceutically acceptable salts.

6. The compound of claim 1 wherein $R_1$ is phenyl.

7. The compounds of claim 1 wherein $R_1$ is halogenophenyl, trifluoromethylphenyl, lower alkyl-phenyl or lower alkoxy-phenyl.

8. The compound of claim 1 wherein $R_1$ is phenyl-lower alkyl.

9. A pharmaceutical composition which comprises a pharmaceutically acceptable carrier, and in a therapeutically effective amount, the compound of claims 1, 2, 3, 4, or 5, which composition has an antagonistic action towards benzodiazepines.

10. A composition as claimed in claim 9, which contains from 1 to 1000 mg of active principle per dosage unit, mixed with a pharmaceutical excipient or vehicle.

* * * * *